(12) United States Patent
McDougall

(10) Patent No.: US 7,389,557 B2
(45) Date of Patent: Jun. 24, 2008

(54) TOOTHBRUSH

(75) Inventor: Gregory McDougall, Angeles (PH)

(73) Assignee: Colgate-Palmolive Company, New York, NY (US)

(*) Notice: Subject to any disclaimer, the term of this patent is extended or adjusted under 35 U.S.C. 154(b) by 0 days.

(21) Appl. No.: 11/328,904

(22) Filed: Jan. 10, 2006

(65) Prior Publication Data

US 2006/0107474 A1 May 25, 2006

Related U.S. Application Data

(63) Continuation of application No. 10/373,738, filed on Feb. 27, 2003, now Pat. No. 6,983,507.

(51) Int. Cl.
*A47L 13/12* (2006.01)
*A46B 13/00* (2006.01)
*A61C 17/16* (2006.01)

(52) U.S. Cl. .................. 15/110; 15/28; 15/180

(58) Field of Classification Search ........ 15/28, 15/110, 22.1, 180, 167.1, 22.2, 179; D4/110, D4/116, 118
See application file for complete search history.

(56) References Cited

U.S. PATENT DOCUMENTS

| | | | |
|---|---|---|---|
| 2,080,605 A * | 5/1937 | Duey ................ 15/167.1 |
| 3,195,537 A | 7/1965 | Blasi | |
| 4,571,768 A | 2/1986 | Kawashima | |
| 5,625,916 A | 5/1997 | McDougall | |
| 5,628,082 A | 5/1997 | Moskovich | |
| 5,652,990 A | 8/1997 | Driesen et al. | |
| 6,021,538 A | 2/2000 | Kressner et al. | |
| 6,446,295 B1 | 9/2002 | Calabrese | |
| D487,636 S | 3/2004 | De Salvo et al. | |
| 6,820,299 B2 | 11/2004 | Gavney, Jr. | |
| 6,820,300 B2 | 11/2004 | Gavney, Jr. | |
| D501,605 S | 2/2005 | Brown et al. | |
| 2002/0138926 A1 * | 10/2002 | Brown et al. ............ 15/22.1 |
| 2003/0033680 A1 | 2/2003 | Davies et al. | |
| 2003/0140437 A1 * | 7/2003 | Eliav et al. ............ 15/22.2 |
| 2004/0154112 A1 | 8/2004 | Braun et al. | |
| 2005/0060822 A1 | 3/2005 | Chenvainu et al. | |

FOREIGN PATENT DOCUMENTS

| | | |
|---|---|---|
| GB | 2 371 217 A | 7/2002 |
| WO | WO 03/043459 A2 | 5/2003 |
| WO | WO 2005/032398 A1 * | 4/2005 |

* cited by examiner

*Primary Examiner*—Laura C Guidotti
(74) *Attorney, Agent, or Firm*—Michael J. Wallace, Jr.

(57) ABSTRACT

An electrically driven toothbrush has a brush holder that is arranged to rotationally vibrate and carry a number of bristles interspaced with arcuate membranes. The membranes serve to aid cleaning of the teeth and to polish the teeth surfaces during use of the toothbrush.

20 Claims, 3 Drawing Sheets

TOOTHBRUSH

CROSS-REFERENCE TO RELATED APPLICATIONS

This is a continuation of U.S. application Ser. No. 10/373,738, filed Feb. 27, 2003 now U.S. Pat. No. 6,983,507, the entirety of which is incorporated by reference herein.

BACKGROUND OF THE INVENTION

The invention relates to toothbrushes.

The invention relates more particularly to electrically driven toothbrushes in which brush bristles are arranged to move relative to an elongate toothbrush handle such that the bristles rotate about an axis generally at right angles to a longitudinal axis of the handle. The bristles may rotate completely or preferably oscillate as fully described for example in U.S. Pat. No. 5,625,916.

In certain conditions, the overall cleaning effect of such brushes is not wholly satisfactory, especially for polishing the teeth or removing stains.

It is an object of the invention to overcome or to at least reduce this problem.

SUMMARY OF THE INVENTION

According to one aspect of the invention there is provided an electrically driven toothbrush having an elongate handle and a brush head mounted to a remote end of the handle, a bristle holder rotatably mounted to the brush head to rotate about an axis generally at right angles to the longitudinal axis of the handle, including an array of upstanding bristles interspaced with a number of separate upstanding flexible membranes that are arranged such as to rub against surfaces of teeth during brushing.

The membranes are preferably shorter than at least the longest of the bristles.

Each membrane is preferably arcuate in cross-section and partially surrounds a respective bristle of the bristle array.

Each membrane may be semi-circular in cross-section and positioned between a respective bristle and the rotational axis of the brush holder.

The membranes are preferably evenly distributed about the brush holder axis and each partially surround a respective peripherally sited bristle of the bristle array.

There are typically five membranes and at least ten bristles.

The membranes may be formed of plastic material.

According to another aspect of the invention there is provided a rotatable bristle holder for an electrically driven toothbrush having an array of upstanding bristles interspaced with a number of separate upstanding flexible membranes arranged such as to rub against surfaces of the teeth during brushing.

BRIEF DESCRIPTION OF THE DRAWINGS

An electric toothbrush according to the invention will now be described by way of example with reference to the accompanying drawings in which.

DETAILED DESCRIPTION

Figure 1:
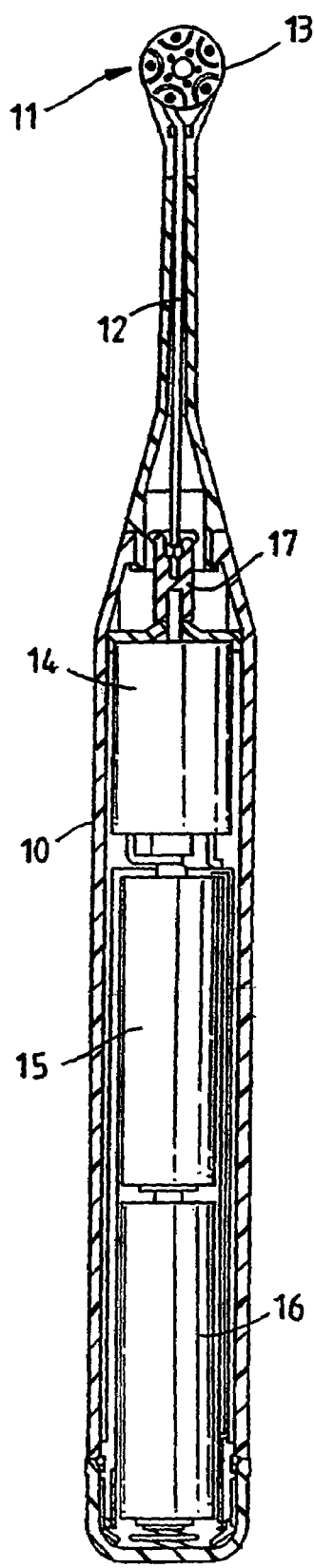
FIG. 1 is a sectional bottom view of the toothbrush.

Referring to the drawings, in FIG. 1 the toothbrush comprises a handle portion 10 at a first end of the toothbrush, a brush head 11 at a second end of the toothbrush, a rotatable shaft 12 extending from the handle to the head, and a generally circular bristle holder 13. The handle provides compartments for holding an electric motor 14 and two batteries 15 and 16. A shaft coupling 17 is arranged to grip one end of the shaft 12 and allow the shaft to be pulled out for cleaning or replacement.

Figure 2:
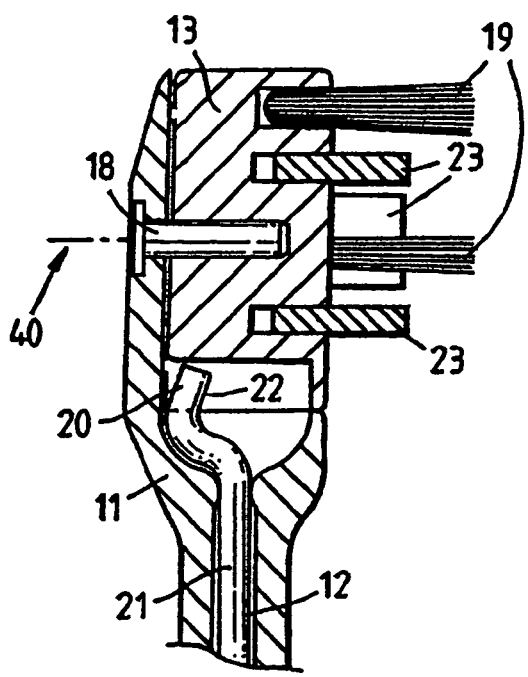
FIG. 2 is a cross-sectional side view of a brush head of the toothbrush.

The head 11, as is better seen in FIG. 2 supports a post 18 which provides a rotational pivot axis 40 for the bristle holder 13. Bristles 19 are shown for illustrative purpose only in FIG. 2. The shaft 12 has an integrally formed remote-most end 20 that is off-set from a central longitudinal axis 21 of the shaft.

Figure 3:
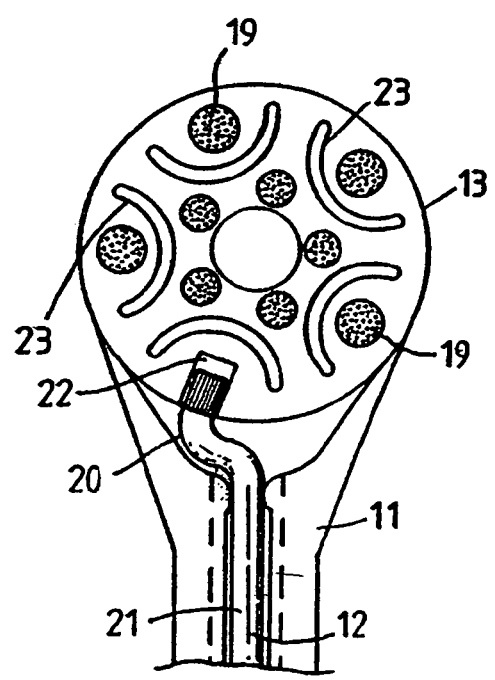
FIG. 3 is a plan view of FIG. 2.

The remote-most end 20 fits a slot 22 (see FIG. 3) formed in a side of the bristle holder 13. It will be noted that the end 20 points towards an intersection of the first axis 21 and a second central axis 40 of the post 18. When the shaft 12 is rotated by the motor 14, the remote end 20 describes a circle about the shaft 12 and drivingly engages the slot 22 to cause the bristle holder 13 to rotationally vibrate. As may be seen in FIG. 3, the slot 22 is closed-ended and extends radially inward from the outer circumference of the holder to less than the distance to the centre of the holder. Thus, the holder 13 pivots or rotates forwards and backwards about the centre of the post 18. Such vibrations comprise the relative motion between the head 11 and the bristles 19 and is generally beneficial for efficient cleaning of teeth. The width of the slot 22 is preferably generally the same as the diameter of the end 20 to leave minimum play; this keeps noise to a minimum in use.

FIG. 1 shows a toothbrush where the holder 13 vibrates or rotates through an angle of 30°. In FIG. 2 the angle is 35°. It will therefore be appreciated that the rotational angle can be chosen by fitting different shafts 12 and that the same bristle holder can be used for all angles. It is also possible to use the holder 13 in a toothbrush where the holder is oscillated through 60° or 120° or rotated through 360° in continuous rotation.

The described shaft 12 is preferably integrally formed, i.e., a single length of a thin rod and shaped as shown. However, it is possible to arrange for the remote end 20 to be separately formed or provided and fixed to a straight end part of the shaft. Such a separate part can be a brush having a central axis coinciding with the axis 21 of the shaft and an off-centre driving post. The driving post then takes up the position and function of the remote end 20. Thus, the driving post and the slot 22 then form the driving engagement between the shaft and the holder 13 and so the driving post can be regarded as the remote end of the shaft.

Figure 4:
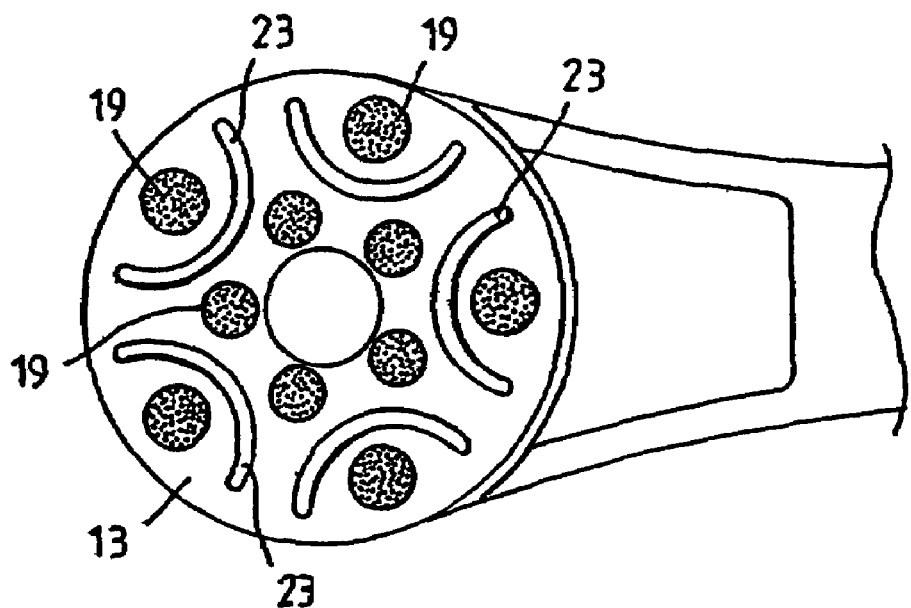
FIG. 4 is an enlarged top plan view of the brush head.
Figure 5:
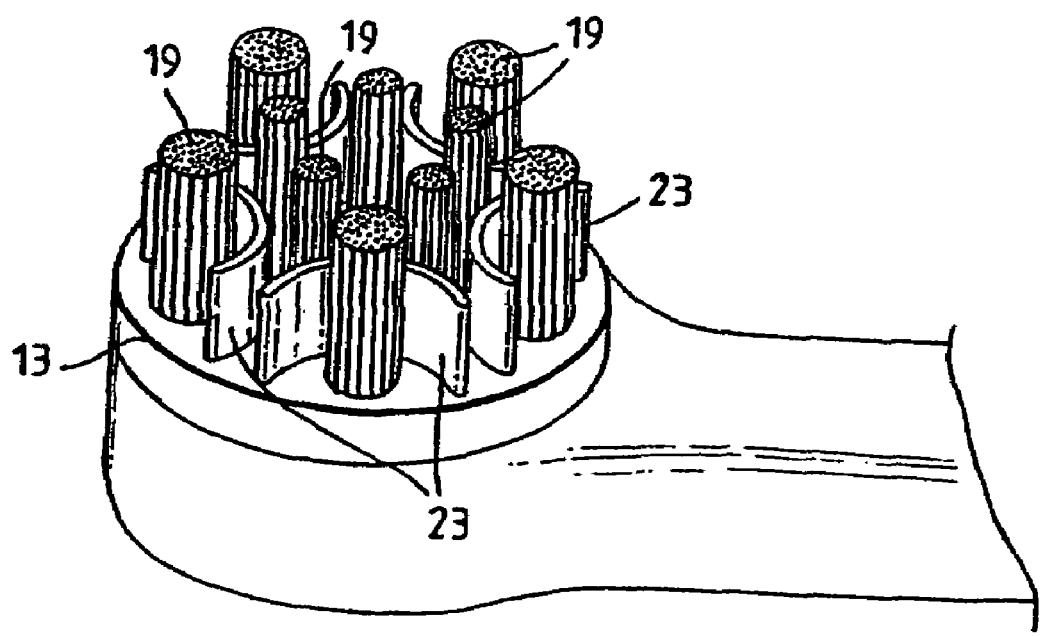
FIG. 5 is an isometric view of FIG. 4.

As shown in FIGS. 4 and 5, the brush holder 13 carries ten bristles that are interspaced by five flexible membranes 23. Each membrane is generally semi-circular in cross-section and partially surrounds a respective bristle mounted adjacent the periphery of the brush holder. The membranes 23 are positioned between the respective bristles and the central axis 40 of the brush holder. In such a configuration, the membranes are inherently unlikely to become clogged up with toothpaste or debris removed from the teeth.

The peripheral bristles are preferably thicker than the inner bristles which may be shorter in length than the peripheral bristles. The membranes 23 are generally shorter than all the bristles and typically protrude up about 50% to 90% of the height of the bristles they partially surround. The membranes are formed of food-safe plastics material such as neoprene or other synthetic rubber, but may be made of woven fabric or similar.

The membranes rub against the surfaces of the teeth and serve to polish surfaces of the teeth and remove stains during use. The membranes may be reasonably effective in this respect if they are generally rectangular in cross-section, or completely or more completely, surround than shown in the Figures, some or all of the bristles.

What is claimed is:

1. A head for a power toothbrush comprising:
    a) a central section and an outer periphery;
    b) a plurality of first tufts of bristles arranged adjacent the outer periphery, each first tuft having a first cross-sectional dimension taken transverse to a longitudinal axis of the first tuft;
    c) a plurality of second tufts of bristles arranged in the central section, each second tuft having a second cross-sectional dimension taken transverse to a longitudinal direction of the second tuft that is different than the first cross-sectional dimension; and
    d) a plurality of arcuate elastomeric elements having portions arranged adjacent the outer periphery and a height different from at least one of a height of the first tufts and a height of the second tufts; wherein the central section is free of elastomeric elements and each elastomeric element at least partially surrounds one of the first tufts.

2. The head of claim 1, wherein the head is round.

3. The head of claim 2, wherein a first tuft is positioned between two elastomeric element portions adjacent the outer periphery.

4. The head of claim 3, wherein the first cross-sectional dimension is larger than the second cross-sectional dimension.

5. The head of claim 4, wherein the first tufts are taller relative to the head than the second tufts.

6. The head of claim 5, wherein the first tufts are the tallest tufts on the head.

7. The head of claim 6, wherein the head comprises four first tufts, four second tufts and four elastomeric cleaning elements.

8. The head of claim 1, wherein the first cross-sectional dimension is larger than the second cross-sectional dimension.

9. The head of claim 1, wherein the first tufts are taller relative to the head than the second tufts.

10. The head of claim 1, wherein the first tufts are the tallest tufts on the head.

11. A power toothbrush comprising:
    a) a round head comprising an outer surface, a central section and an outer periphery;
    b) a drive for oscillating the head about an axis normal to the outer surface;
    c) a plurality of first tufts of bristles arranged adjacent the outer periphery, each first tuft having a first cross-sectional dimension taken transverse to a longitudinal axis of the first tuft;
    d) a plurality of second tufts of bristles arranged in the central section, each second tuft having a second cross-sectional dimension taken transverse to a longitudinal axis of the second tuft that is different than the first cross-sectional dimension; and
    e) a plurality of arcuate elastomeric elements having portions arranged adjacent the outer periphery and a height different from at least one of a height of the first tufts and a height of the second tufts; wherein the central section is free of elastomeric elements and each elastomeric element at least partially surrounds one of the first tufts.

12. The power toothbrush of claim 11, wherein a first tuft is positioned between two elastomeric element portions adjacent the outer periphery.

13. The power toothbrush of claim 12, wherein the first cross-sectional dimension is larger than the second cross-sectional dimension.

14. The power toothbrush of claim 13, wherein the first tufts are taller relative to the head than the second tufts.

15. The power toothbrush of claim 14, wherein the first tufts are the tallest tufts on the head.

16. The power toothbrush of claim 15, wherein the head comprises four first tufts, four second tufts and four elastomeric cleaning elements.

17. The power toothbrush of claim 11, wherein the first cross-sectional dimension is larger than the second cross-sectional dimension.

18. The power toothbrush of claim 11, wherein the first tufts are taller relative to the head than the second tufts.

19. The power toothbrush of claim 11, wherein the first tufts are the tallest tufts on the head.

20. The power toothbrush of claim 11, wherein the head comprises four first tufts, four second tufts and four elastomeric cleaning elements.

* * * * *